United States Patent [19]

Green

[11] 4,331,277
[45] May 25, 1982

[54] SELF-CONTAINED GAS POWERED SURGICAL STAPLER

[75] Inventor: David Y. Green, Norwalk, Conn.

[73] Assignee: United States Surgical Corporation, Norwalk, Conn.

[21] Appl. No.: 152,758

[22] Filed: May 23, 1980

[51] Int. Cl.³ .................... B25C 5/04; A61B 17/04
[52] U.S. Cl. .................... 227/19; 74/110; 227/8; 227/130; 227/DIG. 1; 128/334 R
[58] Field of Search .......... 74/110, 518; 220/89 A; 227/DIG. 1, 8, 19, 83, 155, 130; 128/234 R

[56] References Cited

U.S. PATENT DOCUMENTS

| | | | |
|---|---|---|---|
| 1,732,997 | 10/1929 | White | 74/516 |
| 1,951,224 | 3/1934 | Von Oberstadt | 74/516 |
| 2,058,541 | 10/1936 | Wilshusen | 74/516 |
| 2,076,965 | 4/1937 | Sawtelle | 74/516 |
| 2,103,742 | 12/1937 | Carr | 121/118 |
| 2,165,985 | 7/1939 | Schwentler | 74/516 |
| 2,225,220 | 12/1940 | Huff | 220/89 |
| 2,251,267 | 8/1941 | Carlbom | 188/198 |
| 2,336,490 | 12/1943 | Lo Vico | 220/89 |
| 2,361,810 | 10/1944 | Bazley | 74/110 |
| 2,440,462 | 4/1948 | Cooper | 220/85 |
| 2,487,475 | 11/1949 | Powers | 227/155 |
| 2,496,344 | 2/1950 | Hall | 74/110 |
| 2,767,400 | 10/1956 | Haberstump | 227/155 |
| 3,049,712 | 8/1962 | Khan | 227/DIG. 1 |
| 3,145,874 | 8/1964 | Webb | 220/89 |
| 3,155,271 | 11/1964 | Summers et al. | 220/89 |
| 3,160,890 | 12/1964 | Lefebvre | 227/155 |
| 3,241,713 | 3/1966 | Clapp et al. | 222/5 |
| 3,287,955 | 11/1966 | Winslow et al. | 72/407 |
| 3,294,277 | 12/1966 | Wood | 220/89 |
| 3,515,309 | 6/1970 | Welch | 220/89 |
| 3,613,507 | 10/1971 | Smith | 91/398 |
| 3,618,842 | 11/1971 | Bryan | 227/138 |
| 3,638,652 | 2/1972 | Kelley | 227/19 X |
| 3,643,851 | 2/1972 | Green et al. | 227/19 |
| 3,650,453 | 3/1972 | Smith Jr. 227 | 138/ |
| 3,653,117 | 4/1972 | Wolfberg et al. | 29/429 |
| 3,662,939 | 5/1972 | Bryan | 227/19 |
| 3,680,743 | 8/1972 | Reinnagel | 222/397 |
| 3,684,237 | 8/1972 | Hyde et al. | 251/58 |
| 3,685,686 | 8/1972 | Raidl | 220/89 A |
| 3,717,294 | 2/1973 | Green | 227/19 |
| 3,815,476 | 6/1974 | Green et al. | 227/130 X |
| 3,827,449 | 8/1974 | Gurizzan et al. | 220/89 A X |
| 3,837,555 | 9/1974 | Green | 227/130 |
| 3,872,874 | 3/1975 | Nedelec et al. | 220/89 A X |
| 3,955,581 | 5/1976 | Spasiano et al. | 227/DIG. 1 X |
| 4,043,211 | 8/1977 | Romanenko et al. | 74/110 |
| 4,119,236 | 10/1978 | Shaw et al. | 220/89 A |
| 4,158,422 | 6/1979 | Witten et al. | 220/89 A |
| 4,202,480 | 5/1980 | Annett | 227/8 |
| 4,204,623 | 5/1980 | Green | 227/19 |

OTHER PUBLICATIONS

"Instruction Manual for Auto Suture® Shin and Fascio Stapling Instrument and Disposable Loading Units", United States Surgical Corporation, Aug. 1971.
*Mechanical Design and Systems Handbook*, Rothbart, H. A., McGraw-Hill, 1964, New York, pp. 4–6.

*Primary Examiner*—Paul A. Bell
*Attorney, Agent, or Firm*—Robert R. Jackson; John E. Nathan

[57] ABSTRACT

A surgical stapler powered by a relatively low pressure gas supply contained in the stapler. The stapler has a mechanical linkage between the pneumatic actuator and the staple driver with a differential mechanical advantage to match the substantially constant force provided by the pneumatic actuator to the different forces required to first advance and then form the staple. This mechanical linkage allows use of a relatively small low pressure actuator and also substantially increases the efficiency with which the gas supply is utilized.

40 Claims, 18 Drawing Figures

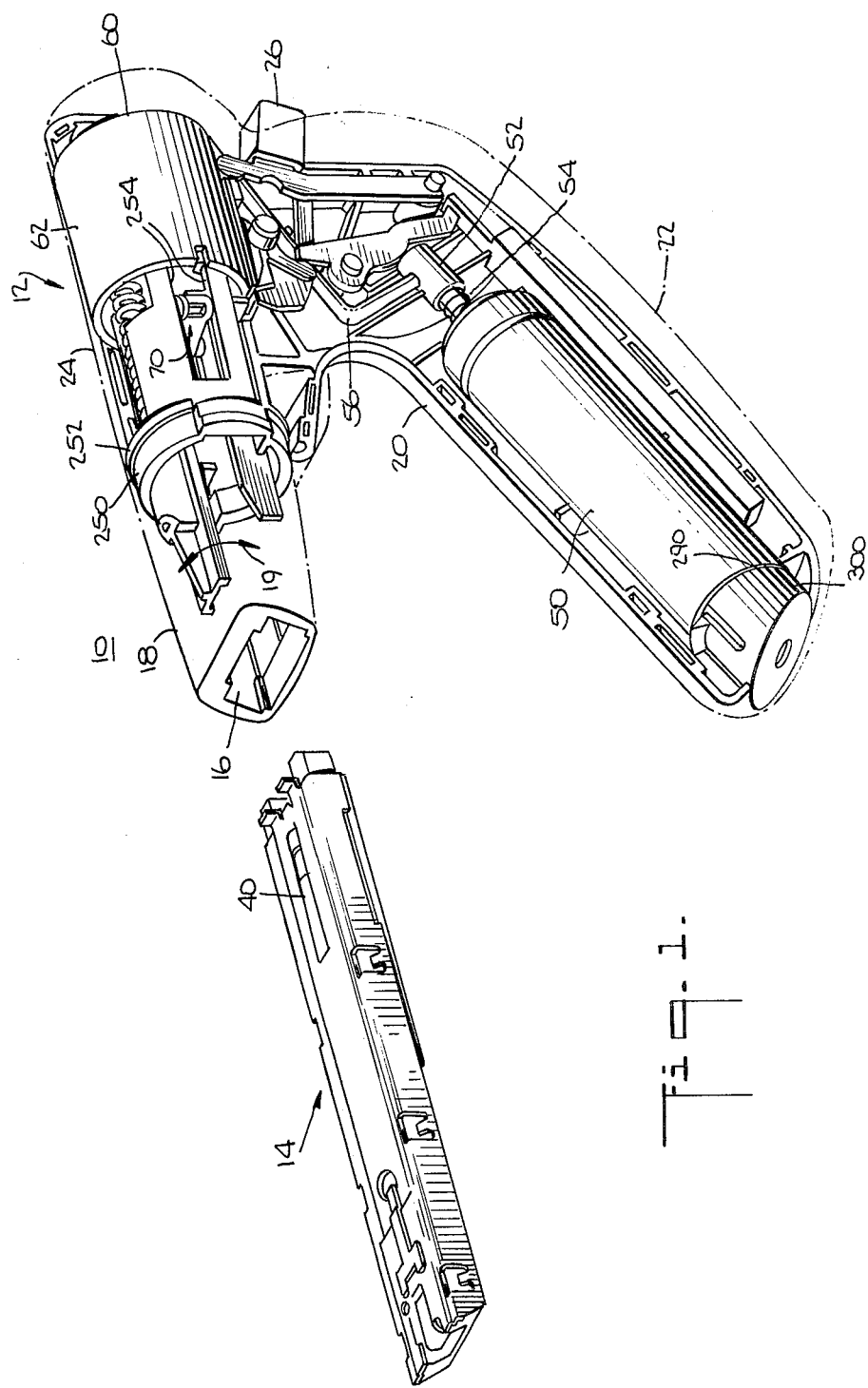

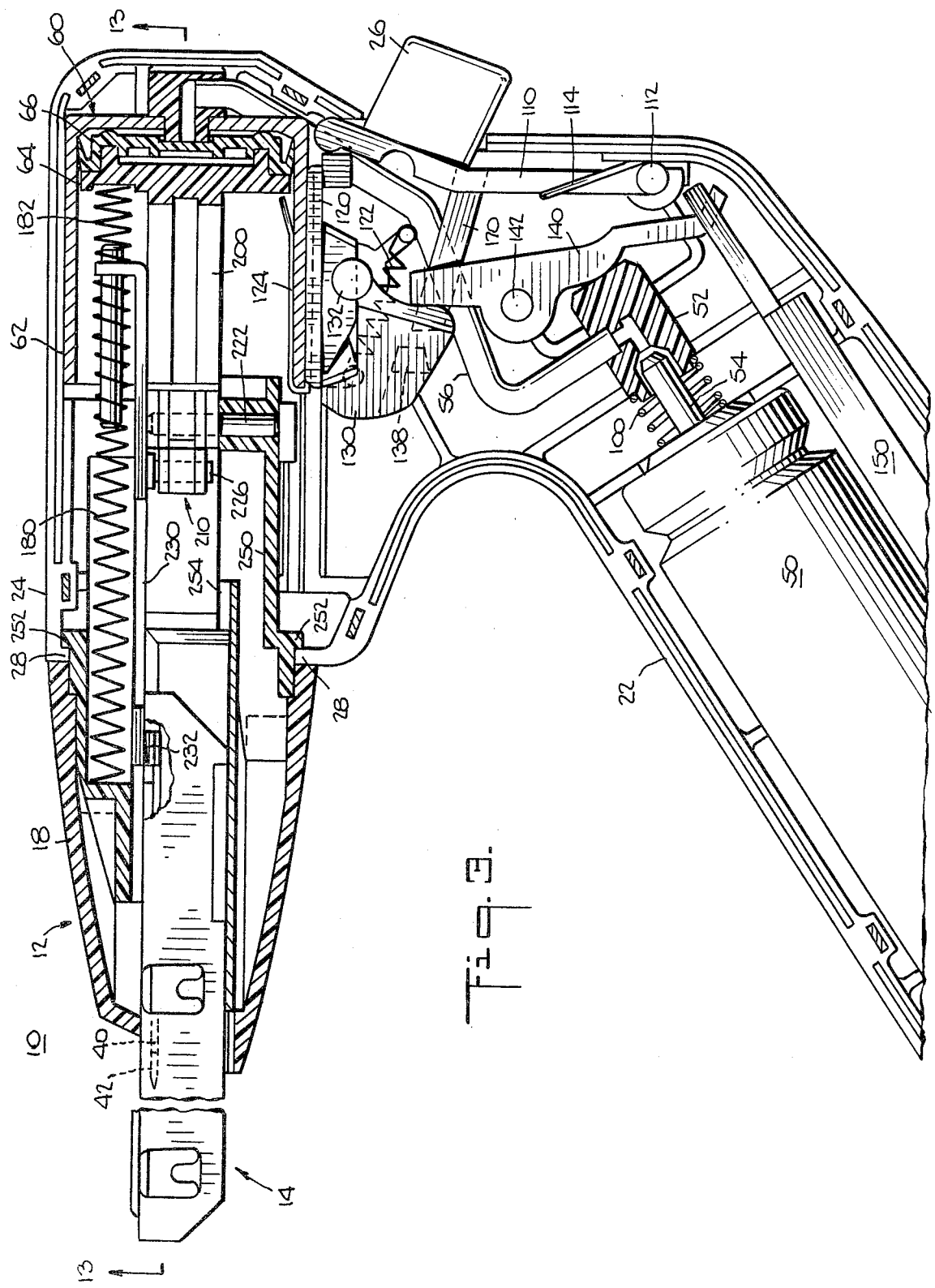

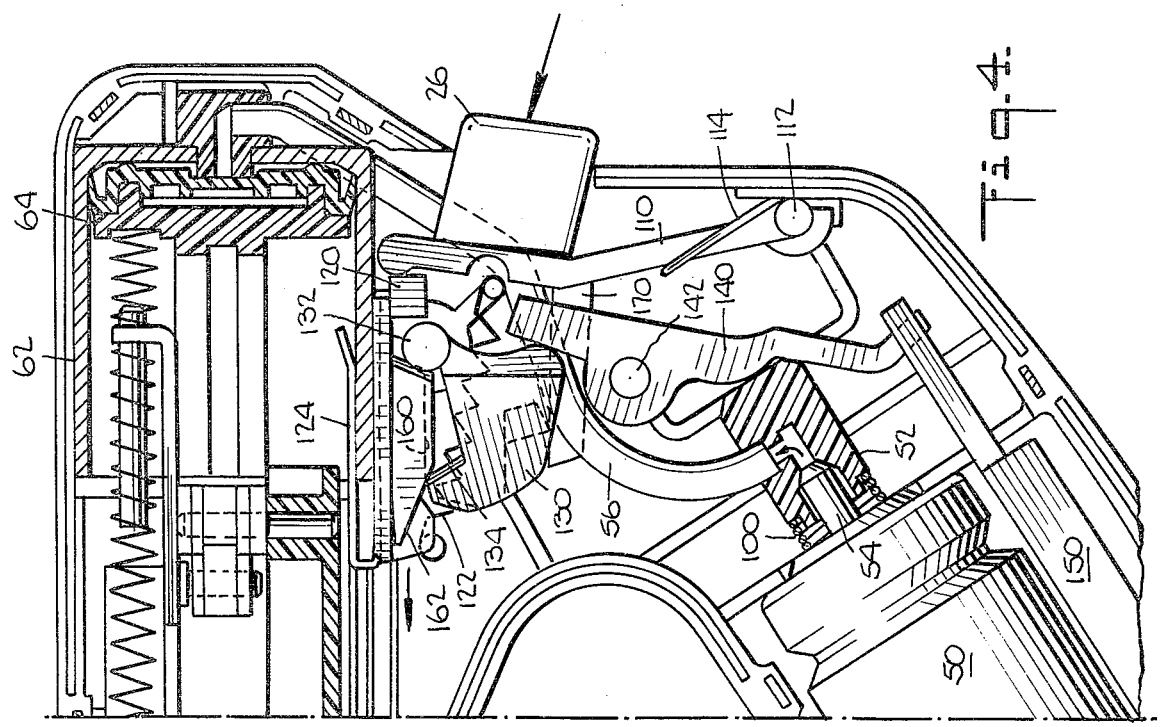
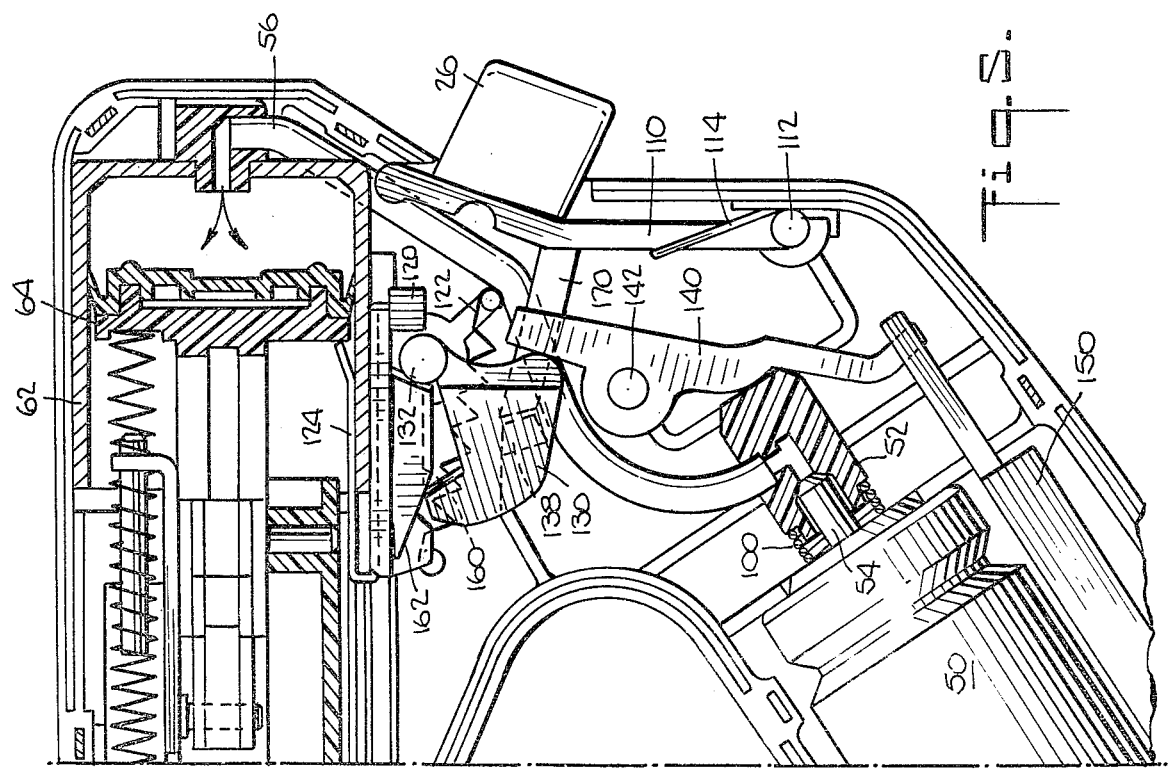

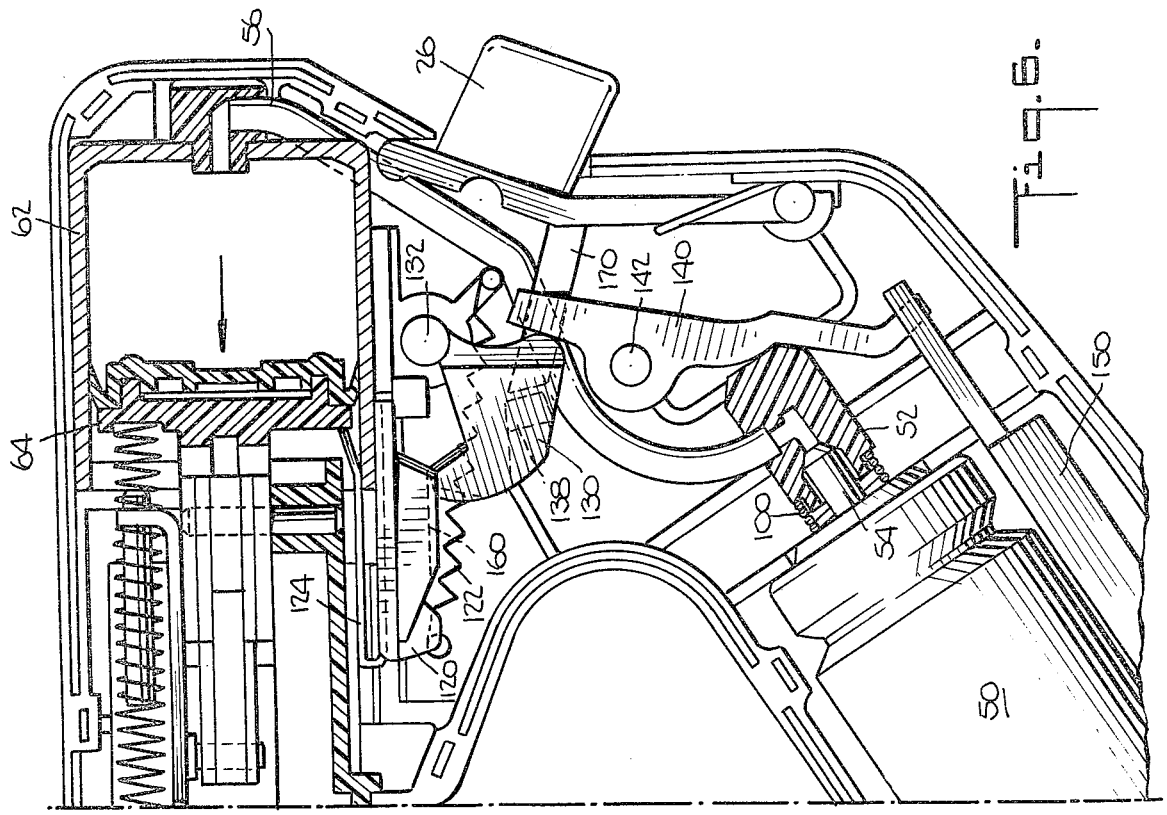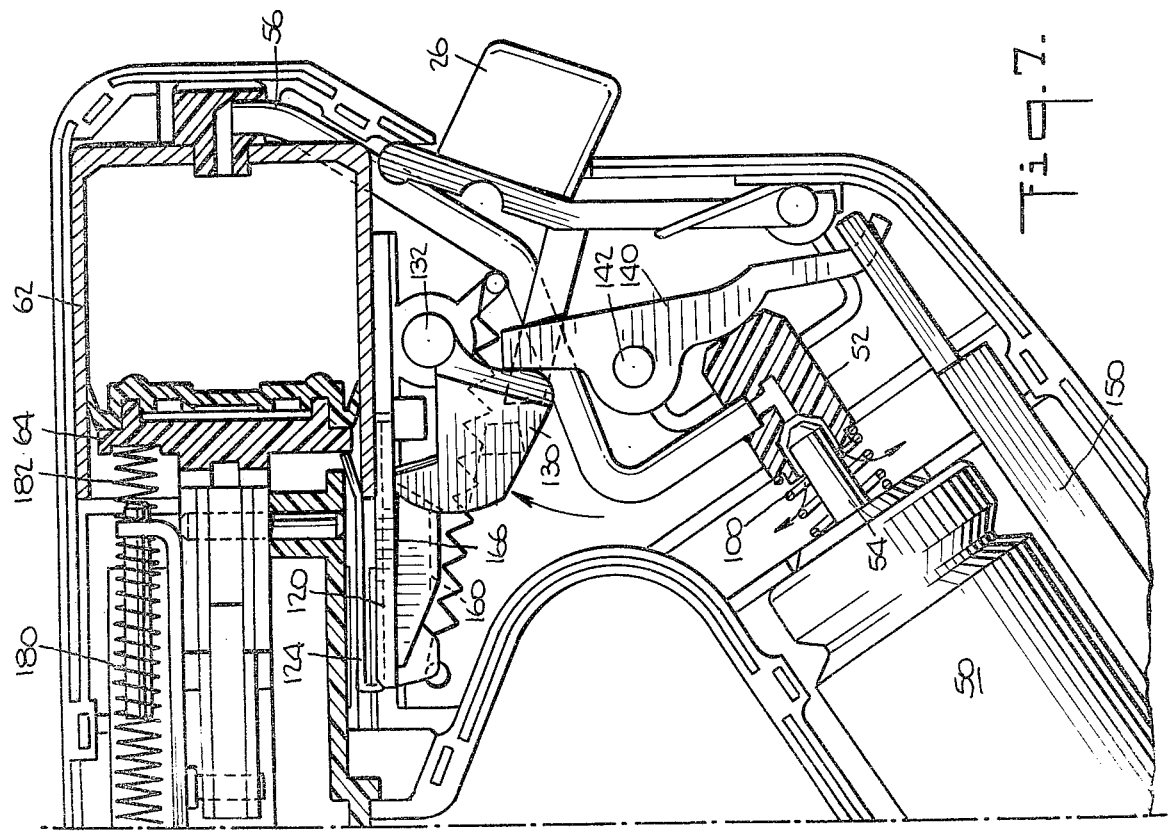

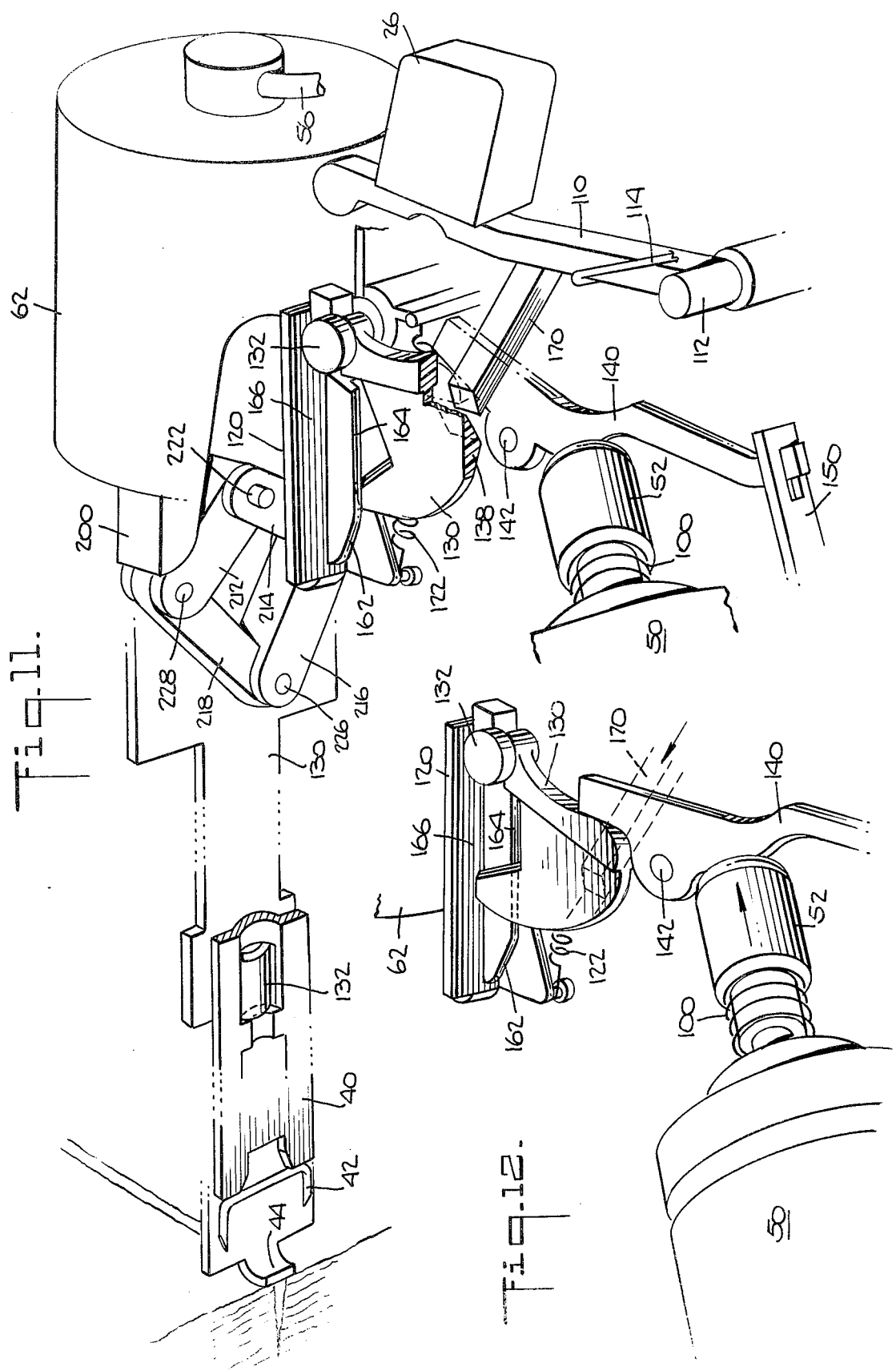

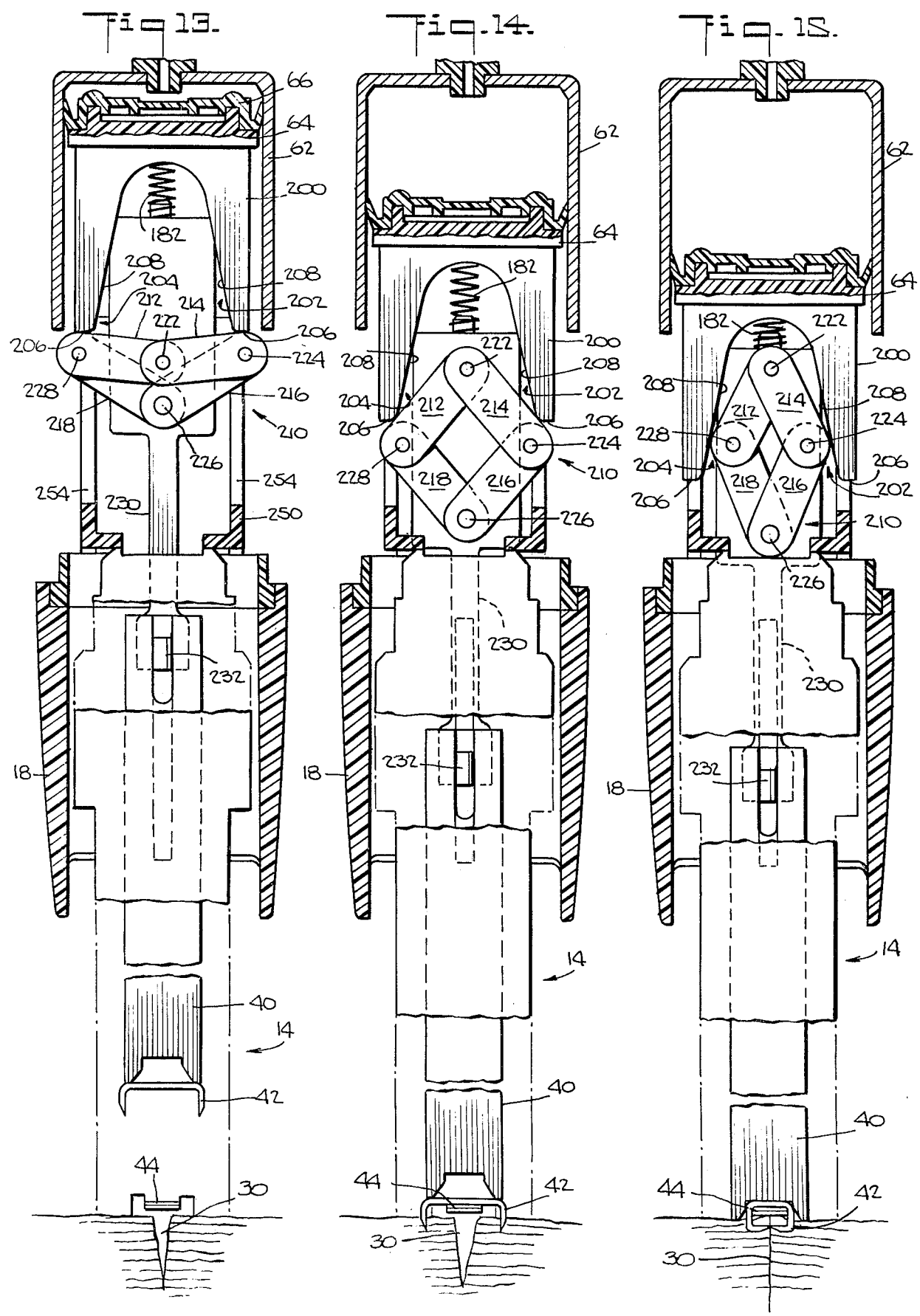

SELF-CONTAINED GAS POWERED SURGICAL STAPLER

BACKGROUND OF THE INVENTION

This invention relates to self-contained gas powered surgical staplers, and more particularly to a self-contained surgical stapler which is powered by relatively low pressure gas and which is therefore adaptable for manufacture as a disposable item. Although the invention will be illustrated and described in its application to skin and fascia type surgical staplers, it will be understood that the principles of the invention are applicable to other surgical stapler type instruments such as ligating and dividing instruments in which staple-like elements are advanced and formed as part of the operation of the instrument.

Self-contained gas powered surgical staplers are known, as shown, for example, in U.S. Pat. Nos. 3,618,842; 3,643,851; 3,662,939; 3,717,294; 3,815,476; and 3,837,555. Typically, these staplers include a replaceable cylinder which supplies gas (e.g., carbon dioxide or nitrogen) at relatively high pressure (e.g., 800 p.s.i.g.) for powering the instrument. The high pressure gas used in these staplers requires that the staplers be of relatively heavy construction which can safely accommodate the high pressures involved. Because of their construction, these instruments are relatively expensive to manufacture. These instruments are therefore generally intended to be relatively permanent and reusable.

Any reusable surgical instrument must be cleaned and sterilized between uses. Cleaning is time consuming and may require disassembly of the instrument with the consequent possibility of damage to the instrument. Sterilization requires expensive sterilization equipment. The trend is therefore increasingly toward instruments which have lower initial cost than permanent instruments, are sterile when purchased, and are disposable after a single use so that cleaning and sterilization costs are avoided.

It is accordingly an object of this invention to provide a self-contained gas powered surgical stapler which can be economically manufactured and safely handled as a disposable item.

Use of a relatively low pressure gas is advantageous to enable a stapler to be made of lighter construction and less expensive materials. This is desirable to lower the cost and make the stapler economically disposable. The stapler must, however, be capable of generating the substantial forces required to form the staples. Typically, the staples are metal wire which is partially formed prior to use and which must be further formed (e.g., bent around or crimped against an anvil) by the stapler. To generate the relatively large forces required to form the staples with low pressure gas would ordinarily require a relatively large pneumatic actuator. This is undesirable because a large actuator makes the stapler bulky and difficult to work with. In addition, a large actuator unnecessarily consumes a large amount of gas during the portion of actuator motion when relatively large forces are not required, i.e., during the first part of the actuator stroke when the staple is merely being advanced to the staple forming position. The gas which is thus effectively wasted substantially reduces the number of stapling operations which can be performed by the stapler before its gas supply is exhausted. This substantially shortens the useful life of the stapler if the gas supply is not replaceable, and even if the gas supply is replaceable, it undesirably increases the frequency with which the gas supply must be replaced.

It is therefore another object of this invention to provide a self-contained gas powered stapler which employs low pressure gas without the necessity for a large pneumatic actuator and which makes efficient use of the gas supply to increase the number of stapling operations which can be performed before the gas supply is exhausted.

SUMMARY OF THE INVENTION

These and other objects of the invention are accomplished in accordance with the principles of the invention by providing a stapler having a mechanical linkage between a relatively low pressure pneumatic actuator and the staple driving element for matching the force available from the pneumatic actuator to the force required during various portions of the stroke of the staple driving element. The mechanical linkage provides a relatively low force during the first portion of the stroke of the staple driving element as is sufficient for advancing a staple to the staple forming position. Thereafter, the mechanical linkage provides the relatively large force required for forming the staple.

During the initial staple advancing portion of the staple driving stroke, the mechanical linkage preferably amplifies the motion of the pneumatic actuator so that the relatively large motion required to advance the staple can be provided by relatively small motion of the actuator. This helps reduce the required length of the actuator stroke and therefore helps reduce the length of the actuator. During the subsequent staple forming portion of the staple driving stroke, the mechanical linkage preferably amplifies the force provided by the pneumatic actuator so that a relatively small diameter actuator can be used with low pressure gas.

Throughout the stroke of the apparatus, the mechanical linkage substantially matches the force required to the force available from the pneumatic actuator. Accordingly, a substantially constant force available from the pneumatic actuator throughout its stroke is converted by the mechanical linkage to the substantially different forces required during the various portions of the stroke of the staple driving element. The pneumatic energy expended during each stroke of the apparatus is therefore not substantially greater than the mechanical work required during that stroke, and the gas supply is used more efficiently to increase the number of stapling operations available from a given quantity of gas.

The stapler of this invention is preferably controlled by a manually operable trigger or other similar control. Momentary operation of the control initiates an operating cycle of the stapler which normally is automatically completed without continued actuation of the control. Preferably the stapler performs only one operating cycle in response to each operation of the control regardless of the length of time the control is operated beyond the time required to initiate an operating cycle. The stapler also cannot begin a new operating cycle until the preceding cycle is complete. In a particularly preferred embodiment of the invention, the operating cycle can be aborted after it has begun by another operation of the control.

Further features of the invention, its nature and various advantages will be more apparent from the accompanying drawing and the following detailed description of the invention.

BRIEF DESCRIPTION OF THE DRAWING

FIG. 3 is a sectional view of the stapler of FIG. 1 prior to the start of a stapler operating cycle.

FIGS. 4–8 are views similar to FIG. 3 showing the condition of the stapler mechanism at various sequential stages in its normal operating cycle.

FIGS. 11 and 12 are partial perspective views of the apparatus shown in FIGS. 3–10 showing operation of the apparatus to interrupt an operating cycle of the stapler.

FIG. 13 is a sectional view taken along the line 13—13 in FIG. 3 and also showing the stapler prior to the start of an operating cycle.

FIGS. 14 and 15 are views similar to FIG. 13 showing the condition of the stapler mechanism at various sequential stages in its operating cycle.

FIG. 16 is a force diagram useful in explaining the operation and advantages of the stapler of this invention.

DETAILED DESCRIPTION OF THE INVENTION

Although the principles of the invention are applicable to other gas powered surgical stapling type instruments such as ligating and dividing instruments in which one or more staple-like elements are first advanced and then formed by the instrument, the invention will be illustratively described in its application to skin and fascia type surgical staplers. Also, although the invention is applicable to surgical staplers having other constructions, the invention will be illustratively described in its application to surgical staplers in which a staple cartridge containing a plurality of staples and including staple advancing and forming elements is mounted in a holder which includes the gas supply, the pneumatic actuator, and control elements. In the particular embodiment shown and described herein the staple cartridge is permanently mounted in the holder. However, it will be understood that the cartridge could be removably mounted in the holder if desired. The staple cartridge will be assumed to be constructed as shown in U.S. Pat. No. 3,650,453 or U.S. Pat. No. 3,717,294. The construction and operation of the staple cartridge forms no part of the present invention and will be referred to herein only to the extent thought necessary to facilitate understanding of this invention.

I. Overall Construction and Operation

Figure 2:
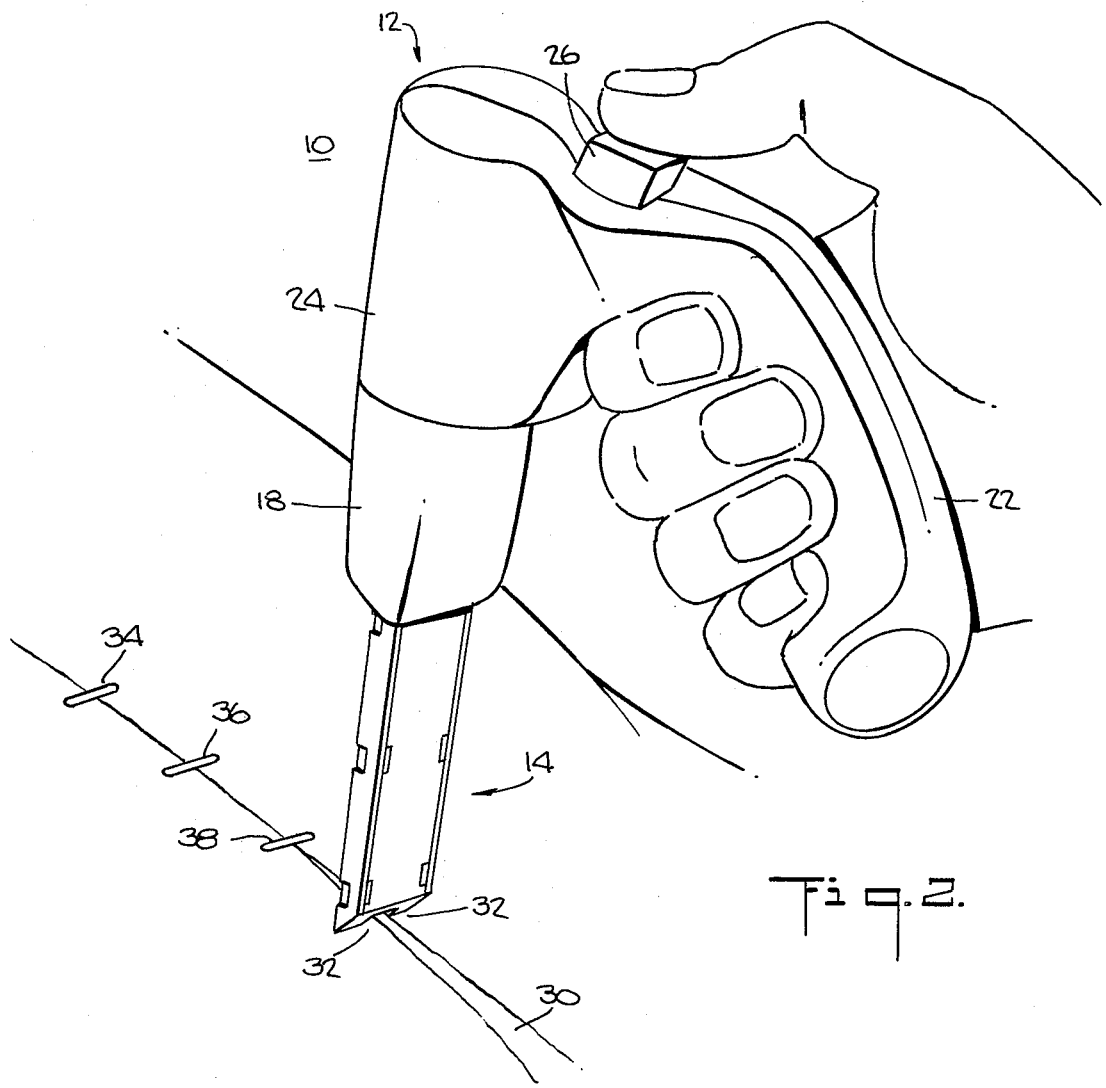
FIG. 2 is a perspective view showing how the stapler of FIG. 1 is held and operated in use.
Figure 1B:
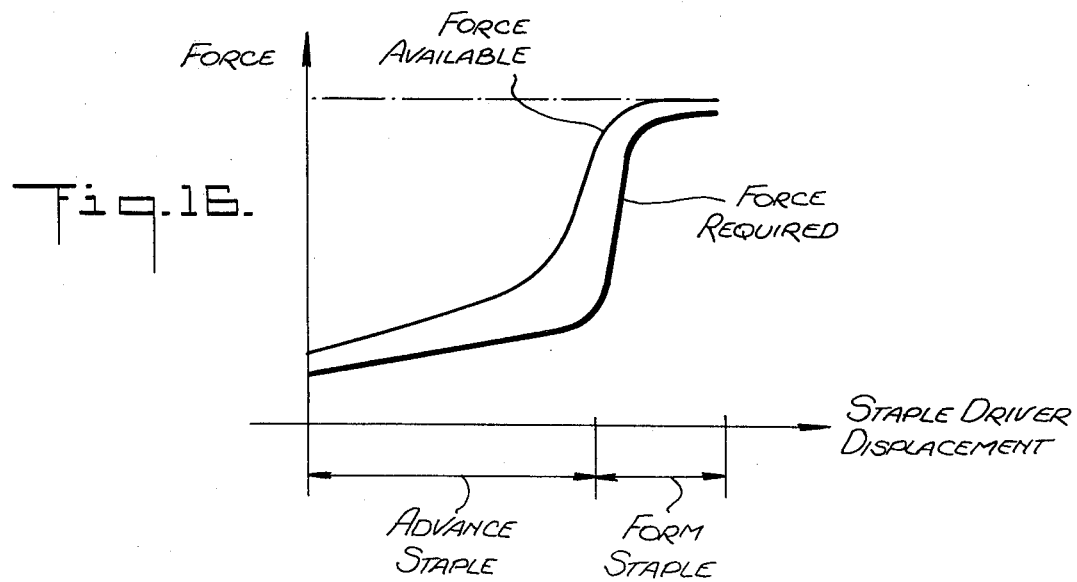
FIG. 1 is a partly exploded overall perspective view of an illustrative embodiment of the surgical stapler of this invention with portions of the housing cut away to reveal the interior of the apparatus.

As shown in FIG. 1, a surgical stapler 10 constructed in accordance with the principles of this invention includes holder 12 and staple cartridge 14. Staple cartridge 14 is shown out of holder 12 in FIG. 1 for clarity, although it is normally mounted in socket 16 in the forward end portion or nose 18 of the barrel 24 of holder 12. As is described in greater detail below, nose 18 and portions of the mechanism inside barrel 24 are rotatable about the longitudinal axis of barrel 24 as indicated by the arrow 19 so that staple cartridge 14 can be rotated to any orientation relative to barrel 24. Holder 12 has an exterior shell or housing 20 (shown cut away to a large extent in FIG. 1), which includes handle portion 22 and barrel portion 24. Handle portion 22 is shaped to fit easily into the hand as shown in FIG. 2. Projecting from housing 20 in a position easily reached by the thumb of the hand holding handle 22 is a push button control 26.

In use as shown in FIG. 2, staple cartridge 14 is mounted in holder 12. Handle 22 is held in the hand with the thumb over push button 26. The stapler is held so that the staple forming distal end of staple cartridge 14 is over the wound or incision 30 to be closed. Typically, this will mean that the staple cartridge is pointing downward. Handle 22 will then also be angled downwardly away from barrel 24 as is most convenient for the user. With the distal end of staple cartridge 14 close to or touching the tissue 32 to be stapled, push button 26 is momentarily depressed. In response, a staple is advanced to the distal end of staple cartridge 14 and then inserted into the tissue and formed into its final shape. In FIG. 2, the stapler is positioned to provide the next staple in a row of staples 34, 36, 38 for closing skin wound 30.

The advancing and forming of a staple is better shown in FIGS. 13–15. At the start of a staple driving stroke as shown in FIG. 13, staple driver 40 in staple cartridge 14 engages staple 42 and advances it toward staple forming anvil 44 at the distal end of the cartridge. When staple 42 reaches anvil 44 as shown in FIG. 14, the pointed ends of staple 42 have entered the tissue to be stapled on respective opposite sides of wound 30. Further motion of staple driver 40 bends or forms staple 42 around anvil 44 as shown in FIG. 15 so that the staple is fully formed and the tissue is pulled and held together to close wound 30.

Returning to FIG. 1 and the general construction of stapler 10, inside the handle portion 22 of holder 12 is a container 50 of relatively low pressure gas. The pressure of the gas in container 50 during operation of the stapler is typically less than 200 p.s.i.g., and preferably in the range from about 30 p.s.i.g. to about 100 p.s.i.g. Any suitable non-toxic gas can be used. Suitable gases include halogenated hydrocarbons which are gaseous at room temperature, e.g., fluorinated hydrocarbons such as Freon 12 or chlorinated hydrocarbons such as Freon 152A. Container 50 dispenses the relatively low pressure gas through stem 54, actuator 52, and conduit 56 when actuator 52 is pressed down on stem 54.

Inside the rear of holder barrel 24 is a pneumatic actuator 60. Actuator 60 includes a pneumatic cylinder 62, which is closed at its rear end (out of sight in FIG. 1) and open at its forward end, and a pneumatic piston 64 (not visible in FIG. 1, but clearly visible in FIG. 3 and subsequent figures) mounted for reciprocal motion in cylinder 62 parallel to the longitudinal axis of barrel 24. For reasons which will be more apparent hereinafter, cylinder 62 is preferably circular in transverse cross section so that piston 64 is rotatable about the longitudinal axis of cylinder 62. As shown, for example, in FIG. 3, piston 64 is pneumatically sealed to cylinder 62 by gasket 66 of molded polyethylene or the like. Gas dispensed from container 50 is supplied to pneumatic actuator 60 via conduit 56 which admits the gas to cylinder 62 behind piston 64 to drive piston 64 forwardly in the cylinder.

Piston 64 is connected to staple driver 40 in staple cartridge 14 via mechanical linkage 70, only partially visible in FIG. 1 but which includes components 200, 210, and 230 shown in other figures and described in detail below. As is explained in more detail below, mechanical linkage 70 matches the force available from pneumatic actuator 60 to the force required to move staple driver 40 through the various portions of its stroke to make more efficient use of the available pneumatic energy.

II. Construction and Normal Operation of the Control Mechanism

As shown, for example, in FIG. 3, dispenser actuator 52 is normally held off the top of stem 54 by compression spring 100 which bears against the top of container 50 and the bottom of actuator 52. Stem 54 is therefore normally not depressed by actuator 52 and no gas flows from container 50. In addition, conduit 56 and pneumatic actuator 60 are normally vented to the atmosphere through the enlarged passageway in actuator 52 around stem 54.

Push button 26 is mounted on lever 110 which is pivoted about axis 112 and normally held outward (to the right as viewed in FIG. 3) by spring 114. The end of lever 110 opposite pivotal axis 112 contacts the rear end of movable cam 120, shown in more detail in FIGS. 9 and 10. Cam 120 is mounted for reciprocal sliding motion along the outer side surface of cylinder 62 and is biased toward the rear by tension spring 122. Cam 120 can be moved forwardly by operation of push button 26, and also moves forward with piston 64 as a result of cam clip 124 which is formed around the side surface of cylinder 62 and which contacts the forward surface of piston 64 at one end and the rear surface of cam 120 at the other end.

Figure 9:
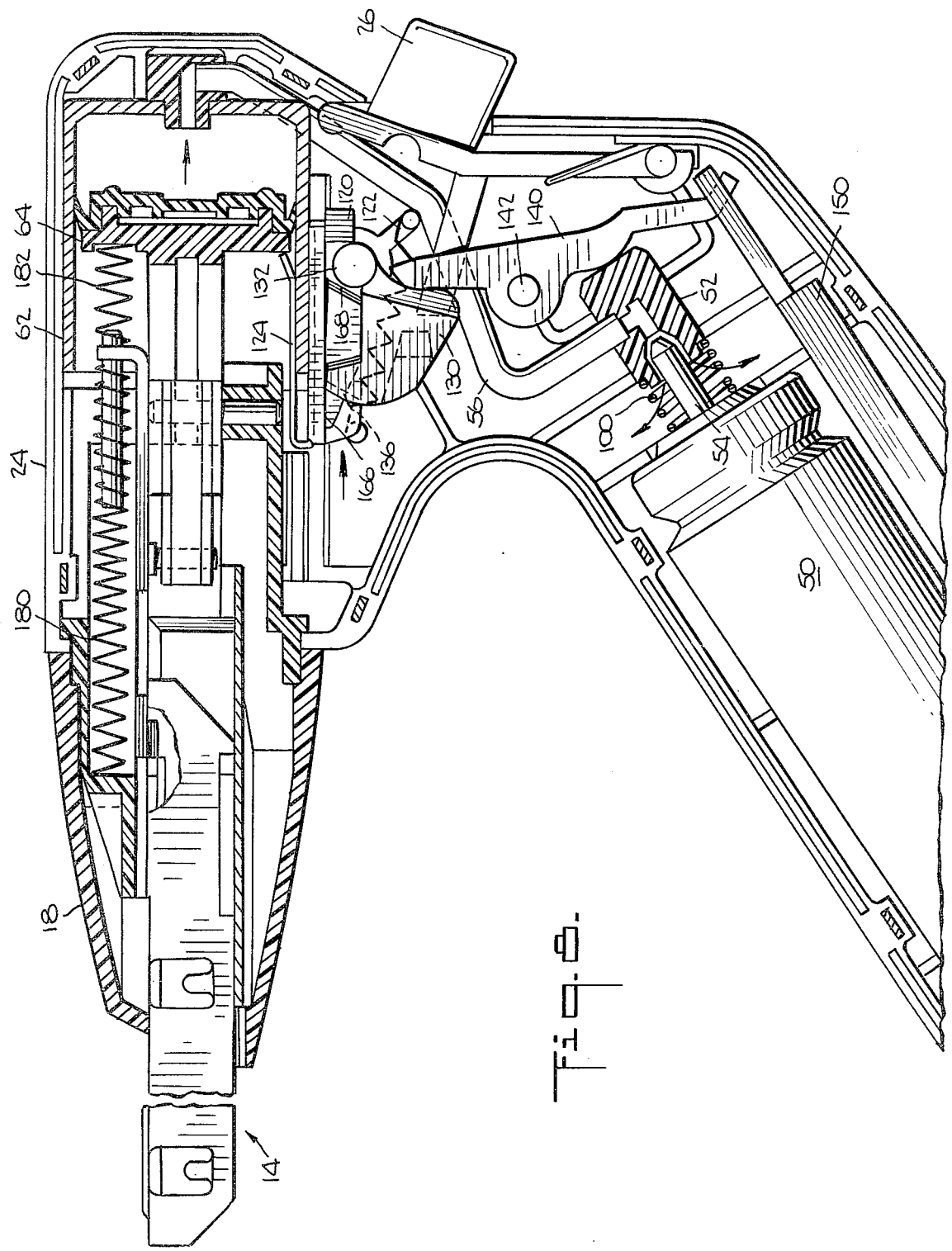
FIGS. 9 and 10 are detailed exploded perspective views of two of the parts shown in FIGS. 3–8.
Figure 9:
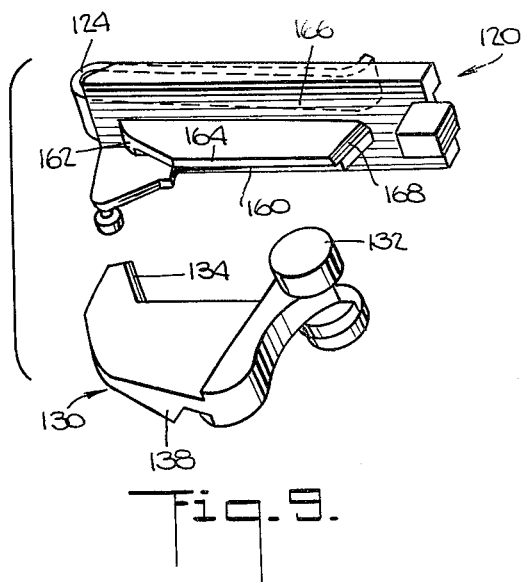
Figure 10:
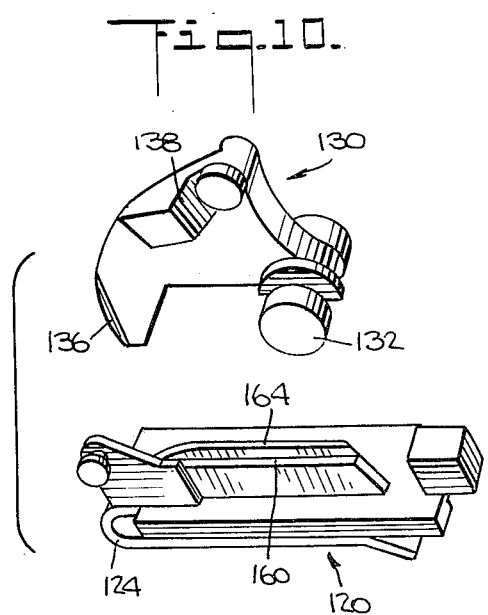

Cam 120 operates on pivoting cam follower 130, also shown in more detail in FIGS. 9 and 10. Cam follower 130 pivots about axis 132. Cam follower 130 is biased against cam 120 by the force of compression spring 100 acting through actuator 52 and lever 140. When cam 120 moves forward, as described in more detail below, cam follower 130 pivots counter-clockwise about axis 132. When thus pivoted, cam follower 130 pivots lever 140 clockwise about its axis 142. Lever 140 then depresses actuator 52, causing pressurized gas to flow from container 50 through conduit 56 into cylinder 62 behind piston 64. The far end of lever 140 is connected to sliding weight 150 which is provided to improve the balance of the instrument and to slow down and quiet the return motion of lever 140 at the end of the pneumatic stroke as described in more detail below.

The trigger or control mechanism just described normally provides a complete pneumatic stroke of the apparatus in response to only momentary operation of push button 26. Push button 26 does not have to be held down throughout the stroke. In addition, the control mechanism provides only one pneumatic stroke in response to each operation of push button 26 even though the push button may be held down longer than is required to initiate a pneumatic stroke. An operating cycle cannot begin until the preceding operating cycle has been completed. The normal sequence of operation of the control mechanism is illustrated in FIGS. 4–8 and will now be described in detail.

In FIG. 4 push button 26 has been depressed by the operator of the instrument. This pivots lever 110 counter-clockwise about axis 112 and initiates forward motion of cam 120 and cam clip 124. As cam 120 moves forward, cam follower 130 rides down the inclined portion 162 of driving stroke cam surface 160 (see also FIGS. 9 and 10). Cam follower 130 is guided into driving stroke cam surface 160 by cooperation of beveled lead-in surface 134 on cam follower 130 and raised rail 164 on cam 120. As cam follower 130 rides down inclined surface 162, it pivots counter-clockwise around axis 132. This in turn pivots lever 140 clockwise about axis 142 and depresses actuator 52. As actuator 52 is depressed, it first compresses spring 100, thereby contacting the top of stem 54 and closing off the vent passageway around the stem. Further depression of actuator 52 depresses stem 54 which allows pressurized gas to flow from container 50 through conduit 56 into cylinder 62 to initiate forward motion of piston 64. Push button 26 need only be operated long enough for piston 64 to reach the position at which it cooperates with cam clip 124 to prevent cam 120 from moving backward enough to allow the system to vent.

In FIG. 5 piston 64 has been driven forward far enough to contact the end of cam clip 124. At this point, cam 120 continues to move forward with piston 64, and push button 26 can be released as shown. Gas continues to flow into cylinder 62 because cam follower 130 continues to depress actuator 52 via lever 140. Accordingly, piston 64 continues to move forward, moving with it cam 120. Cam follower 130 remains pivoted counter-clockwise as it follows the flat portion of driving stroke cam surface 160.

This operation of the apparatus continues until cam follower 130 reaches the rear end of driving stroke cam surface 160 as shown in FIG. 6. Thereafter, further forward motion of cam 120 allows cam follower 130 to drop off the rear end of driving stroke cam surface 160 onto return stroke cam surface 166 as shown in FIG. 7 (see also FIGS. 9 and 10). When cam follower 130 drops onto return stroke cam surface 166, cam follower 130 allows lever 140 to pivot counter-clockwise, thereby releasing actuator 52. This releases stem 54 and stops the flow of gas from container 50. It also vents cylinder 62 through the passageway in actuator 52 around stem 54. Piston 64 therefore begins its return stroke powered by return springs 180 and 182, described below. This repositioning of cam follower 130, lever 140, and actuator 52 at the end of the driving stroke is slowed somewhat by the effect of mass 150 on the motion of lever 140. This tends to quiet the mechanism during what would otherwise be fairly abrupt movements of several parts.

During the return stroke of the apparatus, as shown in FIG. 8, cam 120 travels backward with piston 64 under the influence of tension spring 122. Cam follower 130 bypasses driving stroke cam surface 160 and follows return stroke cam surface 166 as a result of cooperation of lead-in surfaces 136 and 168 on cam follower 130 and cam 120, respectively, at the start of the return stroke (see also FIGS. 9 and 10). At the end of the return stroke, cylinder 62 has been completely vented and all parts of the apparatus are back in their initial positions shown in FIG. 3. The apparatus is accordingly ready to begin another operating cycle in response to another operation of push button 26.

If push button 26 is held down longer than necessary to initiate the driving stroke of the apparatus, the stapler performs normally except that cam 120 does not complete its return motion until push button 26 is released. This is because the end of lever 110 adjacent the rear of cam 120 stops the return motion of cam 120 before that motion is complete. When push button 26 is subsequently released, the return motion of cam 120 resumes the cam 120 returns to its initial position shown in FIG. 3. Until cam 120 has returned to its initial position, the stapler can not begin another operating cycle. Accordingly, the stapler performs only one operating cycle in response to each operation of push button 26, regardless of how long the push button is held down beyond the time required to initiate an operating cycle as described above. Once an operating cycle has been initiated, the stapler is prevented from beginning another operating cycle until push button 26 has been released and the first operating cycle is complete.

III. Construction and Operation of the Abort Mechanism

An additional feature of the control mechanism enables the user of interrupt a staple driving stroke after such a stroke has begun. This is accomplished by a second operation of push button 26 at any time during a driving stroke of piston 64. For this purpose (see, for example, FIGS. 3 and 11), finger 170 is mounted on lever 110 so that it extends to a point on the side of cam follower 130 opposite rail 164 on cam 120 when cam follower 130 is on driving stroke cam surface 160. Near the end of finger 170, cam follower 130 includes a protrusion 138 positioned so that the end of finger 170 misses the protrusion when push button 26 is first operated to initiate a staple driving stroke, but also positioned so that the end of finger 170 hits the protrusion if push button 26 is operated again while cam follower 130 is pivoted counter-clockwise, i.e., while cam follower 130 is on driving stroke cam surface 160. The relative positions of protrusion 138 and the end of finger 170 while cam follower 130 is on driving stroke cam surface 160 are shown in FIGS. 5 and 6, and especially in FIG. 11, which (together with FIG. 12) is intended particularly to illustrate this feature of the invention.

Protrusion 138 and finger 170 are designed so that finger 170 will pass over protrusion 138 without disturbing cam follower 130 when push button 26 is released after a staple driving stroke has been initiated. If, however, push button 26 is operated again during the staple driving stroke, the end of finger 170 firmly contacts protrusion 138, thereby forcing cam follower 130 to jump over rail 164 as shown in FIG. 12 from driving stroke cam surface 160 to return stroke cam surface 166. This immediately stops the staple driving stroke by releasing actuator 52 and venting cylinder 62. With cam follower 130 on return stroke cam surface 166, the apparatus performs as much of a return stroke as is required to return the apparatus to its initial condition. In most instances, the apparatus is not harmed by thus aborting a staple driving stroke and it can be used again simply by re-depressing push button 26.

IV. Construction and Operation of the Staple Driving Mechanism

Details of the staple driving mechanism are best seen in FIGS. 13-15, which also illustrate the operating sequence of this mechanism. As shown in FIG. 13, for example, the staple driving mechanism includes a yoke 200 mounted on the forward surface of piston 64. At its forward open end, yoke 200 has two symmetrical cam surfaces respectively designated by the general reference numbers 202 and 204. Each of these cam surfaces includes a first portion 206 at the end of the yoke. Cam surface portions 206 are preferably substantially perpendicular to the central axis of cylinder 62. Adjacent to portions 206, each yoke cam surface includes a second portion 208 in the cleft of yoke 200. Cam surface portions 208 are synclinal (i.e., inclined toward one another in the direction of the rear of yoke 200), and each portion 208 preferably forms an obtuse angle with the adjacent portion 206.

Mounted forwardly of cylinder 62 is a four bar linkage designated generally by the reference number 210. Four bar linkage includes bars 212, 214, 216, and 218 which are joined at their adjacent ends by hinge or pin connections 222, 224, 226, and 228 (e.g., the adjacent ends of bars 212 and 214 are joined by hinge or pin connection 222; the adjacent ends of bars 214 and 216 are joined by hinge or pin connection 224; and so on around linkage 210). Bars 212 and 214 are both of the same length, and bars 216 and 218 are also both of the same length, which may be the same as or somewhat different from the length of bars 212 and 214. The location of rearmost pin 222 is fixed longitudinally relative to cylinder 62 (see also FIG. 3), preferably in line with the central axis of cylinder 62 and yoke 200. The remaining pins 224, 226, and 228 are free to move longitudinally relative to cylinder 62.

Attached to pin 226 is a push rod 230 (see, also, FIG. 3). Push rod 230 is slidably mounted relative to cylinder 62 so that it can reciprocate parallel to the axis of cylinder 62. As best seen in FIG. 3, main return spring 180 is a compression spring mounted between the rear end of push rod 230 and a forward portion of the cage 250 described below. Secondary return spring 182 is another compression spring mounted between the rear end of push rod 230 and the forward surface of piston 64. The forward end of push rod 230 includes a tongue 232 engaged with a mating recess or aperture near the rear end of staple driver 40 in staple cartridge 14.

Four bar linkage 210, push rod 230, and return spring 180 are all mounted in a generally cylindrical cage 250 best seen in FIGS. 1 and 3. Cage 250 is rotatably mounted in barrel 24 concentric with the longitudinal axis of cylinder 62. Nose portion 18 of barrel 24 is fixed on the forward end of cage 250. Cage 250 is retained in barrel 24 by cooperation of outwardly extending lips 252 on cage 250 and inwardly extending portions 28 on barrel 24. Pin 222 is fixed longitudinally by being mounted in a rear portion of cage 250. The rear portion of cage 250 also includes two longitudinally extending slots 254 through which the portions of four bar linkage 210 adjacent pins 224 and 228 extend outward, at least when the stapler is in its initial condition (see FIG. 13). The forward portions of yoke 200 extend longitudinally into slots 254 behind four bar linkage 210 to contact that linkage as described in detail below. Accordingly, cage 250 and therefore push rod 230, four bar linkage 210, yoke 200, and piston 64 all rotate with staple cartridge 14 and nose 18. Cylinder 62 and the control mechanism do not rotate. The stapler can thus be operated with staple cartridge 14 at any rotational orientation relative to the remainder of the apparatus.

In the initial condition of the staple driving mechanism shown in FIG. 13 (i.e., prior to the application of pneumatic pressure to piston 64), return spring 180 holds push rod 230 in its rearmost position (see also FIG. 3). Push rod 230, acting through pin 226, pushes the portions of four bar linkage 210 adjacent pins 224 and 228 to the rear. These portions of the four bar linkage respectively push on the end portions 206 of yoke cam surfaces 202, 204, thereby pushing piston 64 to the rear. Return spring 182, which has a much lower spring constant than return spring 180 and which never exerts sufficient force to separate yoke 200 from four bar linkage 210, also pushes back on piston 64.

When pressurized gas is admitted to cylinder 62, piston 64 moves forward and the staple driving stroke begins. During the staple driving stroke, the forward motion of piston 64 imparts forward motion to staple driver 40 via the mechanical linkage including yoke 200, four bar linkage 210, and push rod 230. This mechanical linkage has essentially two modes of operation with significantly different mechanical advantage characteristics.

During the first portion of the staple driving stroke when the staple is being advanced from the initial position shown in FIG. 13 to the staple forming position shown in FIG. 14, the end portions 206 of yoke cam surfaces 202 and 204 push on the portions of four bar linkage 210 adjacent pins 224 and 228 in a direction substantially parallel to the direction of motion of piston 64. Accordingly, during this portion of the staple driving stroke four bar linkage amplifies the forward motion of piston 64, so that for each increment of motion of piston 64, push rod 230 moves forward a substantially larger increment. As a concomitant of this amplification of motion, four bar linkage 210 substantially reduces the force applied to push rod 230 as compared to the force exerted by piston 64. The output force of four bar linkage 210 is, however, sufficient to overcome the return spring force and supply the relatively small force required to advance staple 42 to the staple forming position adjacent anvil 44.

As staple 42 reaches anvil 44, the mechanical linkage shifts to its second mode of operation in which the force exerted by piston 64 is substantially amplified to produce the substantially larger force required to form the staple by bending it around anvil 44. This mode of operation continues from the time the staple first reaches the staple forming position as shown in FIG. 14 to the end of the staple driving stroke when the staple is fully formed as shown in FIG. 15. During this mode of operation the inclined portions 208 of yoke cam surfaces 202 and 204 act on the portions of four bar linkage 210 adjacent pins 224 and 228. Accordingly, as piston 64 and yoke 200 advance, inclined yoke cam surfaces 208 act as wedges to push inward on four bar linkage pin connections 224 and 228. This wedge-like action of yoke 200 on four bar linkage 210 substantially amplifies the force of piston 64 as applied to push rod 230. Accordingly, sufficient force is applied to push rod 230 to supply the relatively large force required to form staple 42 around anvil 44, as well as to continue to overcome the return spring force. This amplification of force is accompanied by a reduction in motion. Thus during this portion of the staple driving stroke, each increment of motion of piston 64 produces a substantially smaller increment of motion of push rod 230 and staple driver 40. It should also be noted that during this second portion of the staple driving stroke secondary return spring 182 is gradually compressed.

After completion of the staple driving stroke when cylinder 62 begins to be vented, secondary return spring 182 pushes piston 64 back to initiate the spring powered return stroke of the apparatus. The initial backward thrust on piston 64 provided by return spring 182 relieves the wedging or pinching effect of cam surfaces 208 on four bar linkage 210. This facilitates movement of the portions of four bar linkage 210 adjacent pins 224 and 228 out of yoke 200 as is necessary to allow the staple driving mechanism to return to its initial condition shown in FIG. 13 at the end of the return stroke. Staple driver 40 is then positioned behind another staple 42 ready to begin another cycle of operation.

The differential mechanical advantage provided by the mechanical linkage including yoke 200 and four bar linkage 210 is important to the economical design of the stapler, including its ability to provide the relatively large forces required to form a staple with a relatively small pneumatic actuator 60 supplied with relatively low pressure gas, as well as its efficient use of the gas in its gas supply. These features of the stapler are further illustrated in FIG. 16.

The force required to advance and then form a staple is typically represented as the function of staple driver displacement by the curve labelled "force required" in FIG. 16. As shown by this curve, the force required to advance the staple to the staple forming position (the portion of the staple driving stroke labelled "advance staple" in FIG. 16) is relatively low. The force required to form the staple, however, is relatively high. This is the portion of the staple driving stroke labelled "form staple" in FIG. 16.

The force available from the mechanical linkage in the stapler of this invention is typically represented by the curve labelled "force available" in FIG. 16. This force closely matches the force required to advance and then form the staple during the various portions of the staple driving stroke. In particular, throughout the staple driving stroke the force available is always at least equal to but not substantially greater than the force required. This variable available force is produced by the mechanical linkage from a substantially constant force exerted by piston 64 throughout its driving stroke. This mechanical linkage has a first relatively low and preferably substantially constant value of mechanical advantage during the first or staple advancing portion of the stroke, and a second relatively high and again preferably substantially constant value of mechanical advantage during the second or staple forming portion of the stroke. The constant force exerted by the piston is typically greater than the relatively low force required or available during the staple advancing portion of the stroke, but less than the relatively high force required or available during the staple forming portion of the stroke. Preferably, the pneumatic energy expended during each incremental advance of piston 64 (given by the expression PdV, where P is the pressure of the gas supplied by gas supply 50 and dV is the corresponding incremental change in the volume enclosed by cylinder 62 and piston 64) is approximately equal to the mechanical work performed during the corresponding incremental advance of staple driver 40 (given by the expression Fdx, where F is the force required to advance staple driver 40 and dx is the corresponding incremental advance of the staple driver). Accordingly, substantially all of the pneumatic energy expended in each stroke is converted to required mechanical work, and the available pneumatic energy is used very efficiently.

By way of contrast, if a direct pneumatic drive were used to advance staple driver 40, the pneumatic actuator would have to be sized to provide the maximum required force throughout its entire stroke in order to meet that maximum force requirement. If low pressure gas were used, this would necessitate a pneumatic actuator of much larger diameter than is required in the stapler of this invention. In addition, the curve of force available for such a stapler would be represented by the broken line in FIG. 16, and an amount of pneumatic energy proportional to the area between this line and the curve labelled "force available" would be wasted (as compared to the stapler of this invention) during each staple driving stroke. Similarly, if an indirect drive with a constant value of mechanical advantage were used to make possible the use of a smaller diameter pneumatic actuator, the pneumatic actuator would have to be made much longer than the present actuator and the same amount of pneumatic energy would be wasted during each staple driving stroke.

Thus the stapler of this invention is capable of producing the relatively large forces required to form one or more staples with a relatively small pneumatic actuator supplied with relatively low pressure gas, while at the same time making efficient use of the gas supply. Although the following parameters may vary for different types of instruments and are specified here for purposes of illustration only, the gas pressure is typically as mentioned above, the piston area is typically less than 2 square inches (preferably in the range 0.5 to 1 square inch), and the stroke of the piston is typically less than 2 times the displacement of the staple (preferably in the range from 1 to 2 times the staple displacement).

V. Other Features

As will be apparent from the foregoing, the stapler of this invention can be readily manufactured as a relatively low cost disposable item because of the use of relatively low pressure gas. Thus container 50 and cylinder 62 can be of relatively thin lightweight metal such as aluminum. Most of the remaining parts (with the obvious exception of the springs and the possible exception of a few relatively high stress elements such as push rod 230 which may be metal) can be made of plastic. As a disposable item, the stapler is preferably sold in a sterile condition in packaging designed to keep it sterile until it is used. The stapler is used in a single surgical procedure and then discarded. The user thereby avoids all labor and expense associated with cleaning and sterilizing the instrument.

In a preferred embodiment, gas container 50 is provided with over-pressure relief means for automatically releasing the pneumatic fluid from container 50 in the event that the pressure of the pneumatic fluid exceeds a predetermined threshold level. This threshold level is chosen to be below the pressure at which container 50 would burst or explode. The instrument is thereby made safer, especially when disposed of using high temperatures (e.g., by incineration). Although any of a wide variety of over-pressure relief means such as pressure relief valves can be used, a particularly preferred pressure relief means is illustrated in FIGS. 17 and 18 and described in detail below.

Figure 17:
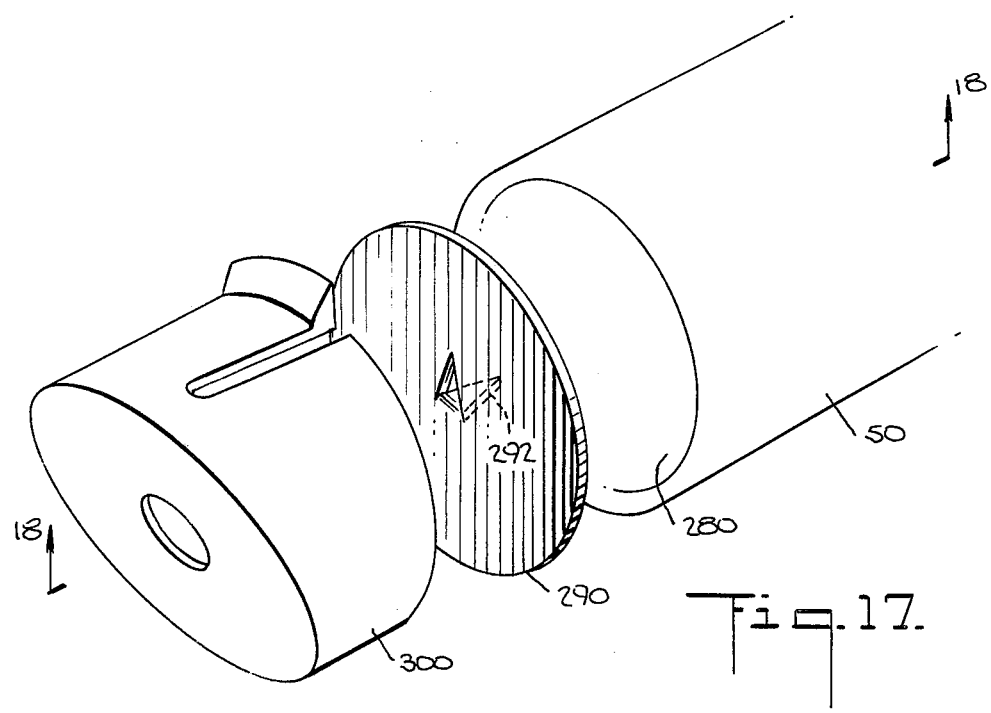
FIG. 17 is a partial exploded perspective view of a particularly preferred embodiment of a portion of the apparatus of FIG. 1.
Figure 18:
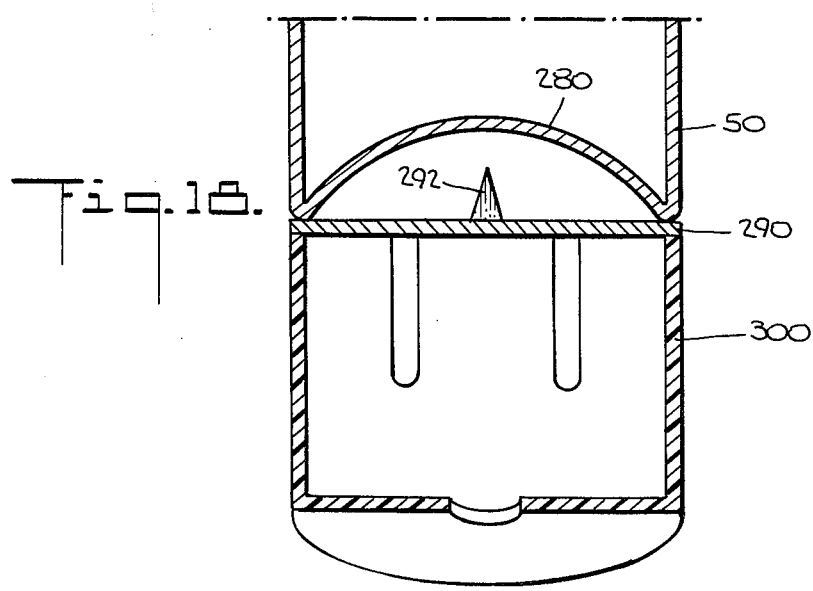
FIG. 18 is a sectional view taken along the line 18—18 in FIG. 17 showing the parts of FIG. 17 assembled.

As shown in FIGS. 17 and 18, container 50 is made with a bottom wall portion 280 which is curved inwardly (i.e., concave) in the center. The periphery of container bottom 280 rests on a peripheral portion of disk 290. Disk 290 is held in place by insert 300 which fits into the butt of handle 22 (see also FIG. 1). Disk 290 is made of a material which is substantially harder and stronger than container bottom 280. For example, if container bottom 280 is aluminum, disk 290 may be iron or steel.

A central portion 292 of disk 290 is partly punched out and bent substantially perpendicular to the plane of disk 290 so that it points toward the concave portion of container bottom 280. The end of punched out portion 292 is sharply pointed. Portion 292 is accordingly referred to for convenience herein as piercer 292.

The end of piercer 292 normally does not touch concave container bottom 280. However, if the pressure in container 50 becomes excessively high, container 50 is designed so that the higher than normal gas pressure in the container causes container bottom 280 to deform outward (i.e., to flatten out or become convex) before container 50 explodes. Container bottom 280 is thus forced into contact with piercer 292, and because piercer 292 is relatively sharp and both stronger and harder than container bottom 280, piercer 292 pierces container bottom 280, thereby allowing the gas in container 50 to escape harmlessly.

Many other arrangements of piercing element 292 are possible. For example, piercing element 292 could be a separate element mounted on disk 290 by welding, soldering, or the like. Piercing element 292 could alternatively be mounted on a structure such as a strap, harness, or cage attached to the sides of container 50.

Although the stapler of this invention is preferably completely disposable, the holder could alternatively be made as a permanent instrument having a replaceable gas supply and accepting disposable staple cartridges.

It will be understood that the foregoing is merely illustrative of the principles of this invention, and that various modifications can be made by those skilled in the art without departing from the scope and spirit of the invention. For example, the stapler need not have the particular overall configuration shown and described herein, but may have any other shape convenient for the user in any intended application. Also, although the stapler shown and described herein is intended for stapling skin and fascia, the stapler could be designed for other surgical procedures such as ligating and dividing.

I claim:

1. Improved gas powered surgical stapling apparatus including a pneumatic piston and a longitudinally reciprocal staple driver for both advancing a staple to a staple forming position and then forming the staple, the staple moving directly with the staple driver during advance of the staple and being bent directly by further motion of the staple driver during forming of the staple, wherein the improvement comprises a mechanical linkage between the pneumatic piston and the staple driver for causing the staple driver to advance more rapidly than the pneumatic piston during the advance of the staple to the staple forming position and for causing the staple driver to advance more slowly than the pneumatic piston during forming of the staple, the mechanical linkage applying a smaller force to the staple driver than the output force of the pneumatic piston while the staple driver is advancing more rapidly than the pneumatic piston, and the mechanical linkage applying a larger force to the staple driver than the output force of the pneumatic piston while the staple driver is advancing more slowly than the pneumatic piston.

2. The apparatus defined in claim 1 wherein the mechanical linkage makes the work performed by the pneumatic pressure applied to the pneumatic piston during each increment of motion of the piston at least equal to but not substantially greater than the work required to cause the associated incremental advance or incremental forming of the staple.

3. The apparatus defined in claim 1 wherein the mechanical advantage of the mechanical linkage changes abruptly from a first value which is less than unity to a second substantially different value which is greater than unity when advance of the staple is substantially complete and forming of the staple is about to begin.

4. The apparatus defined in claim 3 wherein the mechanical advantage of the mechanical linkage is substantially constant at the first value prior to the abrupt change to the second value, and wherein the mechanical advantage of the mechanical linkage is substantially constant at the second value after the abrupt change to the second value.

5. The apparatus defined in claim 1 wherein the source of pressurized gas supplies gas having pressure less than 200 p.s.i.g.

6. The apparatus defined in claim 5 wherein the source of pressurized gas supplies gas having pressure in the range from about 30 p.s.i.g. to about 100 p.s.i.g.

7. Improved gas powered surgical stapling apparatus including a pneumatic piston and a longitudinally movable staple driver for advancing a staple to a staple forming position and then forming the staple, a relatively low force beig required to advance the staple to the staple forming position and a relatively high force being required to form the staple, wherein the improvement comprises a mechanical linkage between the pneumatic piston and the staple driver for producing from a substantially constant force provided by the pneumatic piston throughout its driving stroke the relatively low force required during the advance of the staple to the staple forming position and the relatively high force required during forming of the staple, the mechanical linkage comprising:
    a four bar linkage disposed in a plane parallel to the translational axis of the staple driver and having a first hinge connection attached to the staple driver, an opposite second hinge connection fixed at a point on an axis through the first hinge connection parallel to the translational axis of the staple driver, and third and fourth hinge connections respectively spaced on opposite sides of the axis through the first and second hinge connections; and
    cam means connected to the pneumatic piston and having first and second cam surfaces for respectively operating on the third and fourth hinge connections to push the third and fourth hinge connections substantially parallel to the translational axis of the staple driver during a first portion of the driving stroke of the pneumatic piston corresponding to the advance of the staple and to push the third and fourth hinge connections toward one another during the remainder of the driving stroke of the pneumatic piston corresponding to forming the staple.

8. The apparatus defined in claim 7 wherein each of the first and second cam surfaces comprises a first portion substantially perpendicular to the translational axis of the staple driver for operating on the associated hinge connection during the first portion of the driving stroke of the pneumatic piston and an adjacent second portion which is inclined relative to the translational axis of the staple driver for operating on the associated hinge connection during the second portion of the stroke of the pneumatic piston.

9. The apparatus defined in claim 8 wherein the second portion of each cam surface forms an obtuse angle with the adjacent first portion.

10. Improved gas powered surgical stapling apparatus including a pneumatic piston and a staple driver for advancing a staple to a staple forming position and then forming the staple, a relatively low force being required to advance the staple to the staple forming position and a relatively high force being required to form the staple, wherein the improvement comprises:
    a mechanical linkage between the pneumatic piston and the staple driver for producing from a substantially constant force provided by the pneumatic piston throughout its driving stroke the relatively low force required during the advancce of the staple to the staple forming position and the relatively high force required during forming of the staple;
    a manually operable control;
    means responsive to momentary operation of the manually operable control for normally causing the pneumatic piston to perform one complete cycle of operation including a driving stroke followed by a return stroke which returns the piston to its initial condition; and
    means responsive to operation of the manually operable control during the driving stroke of the pneumatic piston for interrupting the driving stroke and causing the piston to return to its initial condition.

11. The apparatus defined in claim 10 wherein the means responsive to momentary operation of the manually operable control includes means for preventing another cycle of operation from beginning until the manually operable control has been released and the preceding cycle of operation has been completed.

12. Improved gas powered surgical stapling apparatus including a pneumatic piston and a staple driver for advancing a staple to a staple forming position and then forming the staple, a relatively low force being required to advance the staple to the staple forming position and a relatively high force being required to form the staple, wherein the improvement comprises:
    a mechanical linkage between the pneumatic piston and the staple driver for producing from a substantially constant force provided by the pneumatic piston throughout its driving stroke the relatively low force required during the advance of the staple to the staple forming position and the relatively high force required during forming of the staple;
    a manually operable control; and
    means responsive to momentary operation of the manually operable control for normally causing the pneumatic piston to perform one complete cycle of operation including a driving stroke followed by a return stroke which returns the piston to its initial condition, the means responsive to momentary operation of the manually operable control including:
    (a) a movable cam member mounted so that it normally travels with the pneumatic piston and having a driving stroke cam surface and a return stroke cam surface;
    (b) a cam follower for normally engaging the driving stroke cam surface during a driving stroke of the pneumatic piston and the return stroke cam surface during a return stroke of the piston and for causing pneumatic pressure to be applied to the pneumatic piston only while engaged with the driving stroke cam surface; and (c) means for initiating motion of the movable cam member so that the cam follower engages the driving stroke cam surface in response to operation of the manually operable control.

13. The apparatus defined in claim 12 wherein the means responsive to momentary operation of the manually operable control further comprises:

means for preventing the movable cam member from returning to its initial position during the return stroke of the pneumatic piston if the manually operable control is still being operated, thereby preventing initiation of another cycle of operation until the manually operable control has been released and the preceding cycle of operation has been completed.

14. The apparatus defined in claim 12 wherein the improvement further comprises:

means responsive to operation of the manually operable control during the driving stroke of the pneumatic piston for causing the cam follower to leave the driving stroke cam surface and engage the return stroke cam surface to interrupt the driving stroke and cause the piston to return to its initial condition.

15. The apparatus defined in claim 12 wherein the cam follower causes pneumatic pressure to be vented from the pneumatic piston when not engaged with the driving stroke cam surface and wherein the return stroke of the pneumatic piston is powered by return spring means.

16. Improved gas powered surgical stapling apparatus including a pneumatic piston and a longitudinally movable staple driver for advancing a staple to a staple forming position and then forming the staple, a relatively large motion of the staple driver at relatively low force being required to advance the staple to the staple forming position and a relatively small motion of the staple driver at relatively high force being required to form the staple, wherein the improvement comprises a mechanical linkage between the pneumatic piston and the staple driver for producing from a substantially constant force provided by the pneumatic piston throughout its driving stroke the relatively large motion at relatively low force required to advance the staple followed by the relatively small motion at relatively high force required to form the staple, the mechanical linkage comprising:

a toggle mechanism including (a) first and second bars, (b) a first pivotal mounting for the first bar, the first pivotal mounting having a fixed location, (c) a second pivotal mounting for the second bar, the second pivotal mounting being connected to the staple driver, and (d) a pivotal connection between the first and second bars intermediate the first and second pivotal mountings; and a wedge-shaped member connected to the pneumatic piston for operating the toggle mechanism, the wedge-shaped member having an end surface remote from the pneumatic piston and an inclined surface intermediate the end surface and the pneumatic piston, the end surface contacting the toggle mechanism adjacent the pivotal connection to apply a force to that portion of the toggle mechanism substantially parallel to the axis of motion of the staple driver during advance of the staple, and the inclined surface contacting the toggle mechanism adjacent the pivotal connection to apply a force to that portion of the toggle mechanism substantially perpendicular to the axis of motion of the staple driver during formation of the staple.

17. The apparatus defined in claim 16 wherein the mechanical linkage amplifies the motion of the pneumatic piston during the first part of its driving stroke, corresponding to advance of the staple, and amplifies the force of the pneumatic piston during the remainder of its driving stroke, corresponding to forming of the staple.

18. The apparatus defined in claim 16 wherein the improvement further comprises:

a manually operable control; and means responsive to momentary operation of the manually operable control for normally causing the pneumatic piston to perform one complete cycle of operation including a driving stroke followed by a return stroke which returns the piston to its initial condition.

19. The apparatus defined in claim 18 wherein the means responsive to momentary operation of the manually operable control includes means for preventing another cycle of operation from beginning until the manually operable control has been released and the preceding cycle of operation has been completed.

20. The apparatus defined in claim 18 wherein the improvement further comprises:

means responsive to operation of the manually operable control during the driving stroke of the pneumatic piston for stopping the driving stroke and causing the piston to return to its initial condition.

21. The apparatus defined in claim 18 wherein the means responsive to momentary operation of the manually operable control comprises:

a movable cam mounted so that it normally travels with the pneumatic piston and having a driving stroke cam surface and a return stroke cam surface;

a cam follower for normally engaging the driving stroke cam surface during a driving stroke of the pneumatic piston and the return stroke cam surface during a return stroke of the piston and for causing pneumatic pressure to be applied to the pneumatic piston only while engaged with the driving stroke cam surface; and means for initiating motion of the movable cam so that the cam follower engages the driving stroke cam surface in response to operation of the manually operable control.

22. The apparatus defined in claim 21 wherein the means responsive to momentary operation of the manually operable control further comprises:

means for preventing the movable cam from returning to its initial condition during the return stroke of the pneumatic piston if the manually operable control is still being operated, thereby preventing initiation of another cycle of operation until the manually operable control has been released and the preceding cycle of operation has been completed.

23. The apparatus defined in claim 21 wherein the improvement further comprises:

means responsive to operation of the manually operable control during the driving stroke of the pneumatic piston for causing the cam follower to jump from the driving stroke cam surface to the return stroke cam surface to stop the driving stroke of the piston and cause it to return to its initial condition.

24. The apparatus defined in claim 21 wherein the cam follower causes pneumatic pressure to be vented from the pneumatic piston when not engaged with the driving stroke cam surface and wherein the return stroke of the pneumatic piston is powered by return spring means.

25. Improved gas powered surgical stapling apparatus including a pneumatic piston and a staple driver movable parallel to the axis of the pneumatic piston for advancing a staple to a staple forming position and then forming the staple, a relatively large motion of the staple driver at relatively low force being required to advance the staple to the staple forming position and a relatively small motion of the staple driver at relatively high force being required to form the staple, wherein the improvement comprises a mechanical linkage between the pneumatic piston and the staple driver for producing from a substantially constant force provided by the pneumatic piston throughout its driving stroke the relatively large motion at relatively low force required to advance the staple followed by the relatively small motion at relatively high force required to form the staple, the mechanical linkage comprising:

a four bar linkage disposed in a plane parallel to the axis of the pneumatic piston and having a first hinge connection attached to the staple driver, an opposite second hinge connection fixed at a point on an axis through the first hinge connection parallel to the axis of the pneumatic piston, and third and fourth hinge connections respectively spaced on opposite sides of the axis through the first and second hinge connections; and cam surfaces connected to the pneumatic piston for operating on the third and fourth hinge connections to push the third and fourth hinge connections substantially parallel to the axis of the pneumatic piston during a first portion of its driving stroke corresponding to the advance of the staple and to squeeze the third and fourth hinge connections toward one another during the remainder of the driving stroke of the pneumatic piston corresponding to forming of the staple.

26. The apparatus defined in claim 25 wherein the cam surfaces comprise a yoke connected to the pneumatic piston and opening toward the four bar linkage, the yoke having first and second end surfaces substantially perpendicular to the axis of the pneumatic piston for respectively operating on the third and fourth hinge connections during the first portion of the driving stroke of the pneumatic piston and third and fourth synclinal surfaces respectively adjacent the first and second end surfaces for respectively operating on the third and fourth hinge connections during the remainder of the driving stroke of the pneumatic piston.

27. A self-contained gas powered holder for holding and actuating a cartridge containing surgical staples to cause at least one staple to be advanced to a staple forming position and then formed into a completed staple, a relatively low force being required to advance the staple to the staple forming position and a relatively high force being required to form the staple, comprising:

a source of pressurized pneumatic fluid;
a pneumatic cylinder pneumatically connected to the source of pressurized pneumatic fluid;
a pneumatic piston mounted for reciprocal motion in the cylinder; and
a mechanical linkage between the pneumatic piston and the actuatable part of the cartridge for producing from a substantially constant force provided by the pneumatic piston throughout its driving stroke the relatively low force required to cause the cartridge to advance the staple to the staple forming position and then the relatively high force required to cause the cartridge to form the completed staple, the mechanical linkage including:

(1) a longitudinally movable link member coupled to the actuatable part of the cartridge;
(2) a toggle mechanism including (a) first and second bars, (b) a first pivotal mounting for the first bar, the first pivotal mounting having a fixed location, (c) a second pivotal mounting for the second bar, the second pivotal mounting being connected to the link member, and (d) a pivotal connection between the first and second bars intermediate the first and second pivotal mountings; and
(3) cam means connected to the pneumatic piston for slidably contacting a surface of the toggle mechanism to push the pivotal connection in a direction substantially parallel to the axis of motion of the link member during the advance of the staple to the staple forming position and to push the pivotal connection in a direction substantially perpendicular to the axis of motion of the link member during forming of the staple.

28. A self-contained gas powered holder for holding and actuating a cartridge containing surgical staples to cause at least one staple to be advanced to a staple forming position and then formed into a completed staple, a relatively low force being required to advance the staple to the staple forming position and a relatively high force being required to form the staple, comprising:

a source of pressurized pneumatic fluid;
a pneumatic cylinder pneumatically connected to the source of pressurized pneumatic fluid;
a pneumatic piston mounted for reciprocal motion in the cylinder; and
a mechanical linkage between the pneumatic piston and the actuatable part of the cartridge for producing from a substantially constant force provided by the pneumatic piston throughout its driving stroke the relatively low force required to cause the cartridge to advance the staple to the staple forming position and then the relatively high force required to cause the cartridge to form the completed staple, the mechanical linkage including:

(a) a four bar linkage having a first hinge connection coupled to the actuatable part of the cartridge, an opposite second fixed hinge connection, and third and fourth hinge connections respectively spaced on opposite sides of the axis through the first and second hinge connections; and
(b) cam means connected to the pneumatic piston and having first and second cam surfaces for respectively operating on the third and fourth hinge connections to push the third and fourth hinge connections substantially parallel to the axis through the first and second hinge connections when the relatively low force is required and to push the third and fourth hinge connections toward one another when the relatively high force is required.

29. A self-contained gas powered surgical stapler for advancing a staple to a staple forming position and then forming the staple, a relatively low force being required to advance the staple to the staple forming position and a relatively high force being required to form the staple, comprising:

a source of pressurized gas in the stapler;

a pneumatic actuator including a cylinder and a piston reciprocally mounted in the cylinder;

gas conduit means including valve means for selectively conducting pressurized gas from the source of gas to the pneumatic actuator to drive the piston in a driving stroke;

a longitudinally reciprocal staple driver for advancing and forming the staple; and mechanical coupling means between the piston and the staple driver for converting the substantially constant force available from the piston to the relatively low force required to advance the staple to the staple forming position during a first portion of the driving stroke of the piston and to the relatively high force required to form the staple during a second portion of the driving stroke of the piston, the mechanical coupling means including:

(1) a toggle mechanism including (a) first and second bars, (b) a first pivotal mounting for the first bar, the first pivotal mounting having a fixed location, (c) a second pivotal mounting for the second bar, the second pivotal mounting being connected to the staple driver, and (d) a first pivotal connection between the first and second bars intermediate the first and second pivotal mountings; and (2) cam means connected to the pneumatic piston for slidably contacting a surface of the toggle mechanism to push the first pivotal connection in a direction substantially parallel to the reciprocal axis of the staple driver during the advance of the staple to the staple forming position and to push the first pivotal connection in a direction substantially perpendicular to the reciprocal axis of the staple driver during forming of the staple.

30. The apparatus defined in claim 29 wherein the staple driver is rotatable relative to at least a portion of the pneumatic actuator.

31. The apparatus defined in claim 29 wherein the first and second bars comprise two bars of a four bar linkage disposed in a plane parallel to the reciprocal axis of the staple driver, the third and fourth bars of the four bar linkage being pivotally mounted on the first and second pivotal mountings, respectively, and the third and fourth bars having a second pivotal connection intermediate the first and second pivotal mountings, the first and second pivotal mountings being aligned on an axis parallel to the reciprocal axis of the staple driver, the first and second pivotal connections being respectively spaced on opposite sides of the axis through the first and second pivotal connections; and wherein the cam means includes first and second cam surfaces for respectively operating on the first and second pivotal connections to exert forces on the first and second pivotal connections substantially parallel to the reciprocal axis of the staple driver during the first portion of the driving stroke of the piston and to exert forces on the first and second pivotal connections substantially perpendicular to the reciprocal axis of the staple driver during the second portion of the driving stroke of the piston.

32. The apparatus defined in claim 31 wherein each of the first and second cam surfaces comprises a first portion substantially perpendicular to the reciprocal axis of the staple driver for operating on the associated pivotal connection during the first portion of the driving stroke of the piston and an adjacent second portion which is inclined relative to the reciprocal axis of the staple driver for operating on the associated pivotal connection during the second portion of the driving stroke of the piston.

33. The apparatus defined in claim 32 wherein the second portion of each cam surface forms an obtuse angle with the adjacent first portion.

34. The apparatus defined in claim 33 wherein the pneumatic actuator piston is a circular cylinder, wherein the piston is rotatable about its longitudinal axis relative to the pneumatic actuator cylinder, and wherein the mechanical linkage and the staple driver rotate with the piston.

35. The apparatus defined in claim 29 further comprising:

a manually operable control;

means responsive to momentary operation of the manually operable control for operating the valve means to supply pressurized gas to the pneumatic actuator until the driving stroke of the piston is complete and then venting the pneumatic actuator; and return spring means connected to the piston for returning the piston to its initial condition when the pneumatic actuator is vented.

36. The apparatus defined in claim 35 wherein the means responsive to momentary operation of the manually operable control comprises:

a movable cam mounted so that it normally travels with the piston and having a driving stroke cam surface and a substantially parallel return stroke cam surface;

a cam follower for normally engaging the driving stroke cam surface during a driving stroke of the piston and for thereafter engaging the return stroke cam surface, the cam follower operating the valve means to supply pressurized gas to the pneumatic actuator when engaged with the driving stroke cam surface and venting the pneumatic actuator when engaged with the return stroke cam surface; and means for initiating motion of the movable cam member so that the cam follower engages the driving stroke cam surface in response to operation of the manually operable control.

37. The apparatus defined in claim 36 wherein the means responsive to momentary operation of the manually operable control further comprises:

means for preventing the movable cam from returning to its initial condition during the return stroke of the pneumatic piston if the manually operable control is still being operated, thereby preventing initiation of another cycle of operation until the manually operable control has been released and the preceding cycle of operation has been completed.

38. The apparatus defined in claim 36 further comprising:

means responsive to operation of the manually operable control during a driving stroke of the piston for causing the cam follower to leave the driving stroke cam surface and to engage the return stroke cam surface, thereby interrupting the driving stroke of the piston and causing it to return to its initial condition.

39. The apparatus defined in claim 29 wherein the source of pressurized gas includes over-pressure relief means for automatically releasing the pressurized gas from the pressurized gas source when the pressure of the gas in the pressurized gas source exceeds a predetermined threshold value below the pressure at which the pressurized gas source would burst.

40. The apparatus defined in claim 39 wherein the source of pressurized gas is a container having a wall portion which is normally concave inward and which deforms outwardly when the pressure of the gas in the container exceeds the predetermined threshold value, and wherein the apparatus further comprises piercer means disposed adjacent the normally concave inward container wall portion for piercing the container wall portion and releasing the gas when the wall portion deforms outwardly.

* * * * *

UNITED STATES PATENT AND TRADEMARK OFFICE
CERTIFICATE OF CORRECTION

PATENT NO. : 4,331,277
DATED : May 25, 1982
INVENTOR(S) : David T. Green

It is certified that error appears in the above—identified patent and that said Letters Patent is hereby corrected as shown below:

| Column | Line | |
|---|---|---|
| 5 | 34 | Change "forwardly" to --forward--. |
| 7 | 22 | Change "of" to --to--. |
| 12 | 50 | After "staple," (second occurrence) insert --a relatively low force being required to advance the staple to the staple forming position and a relatively high force being required to form the staple,--. |

Signed and Sealed this

Twenty-fifth Day of January 1983

[SEAL]

Attest:

GERALD J. MOSSINGHOFF

Attesting Officer    Commissioner of Patents and Trademarks